US008882477B2

(12) United States Patent
Fritz, IV et al.

(10) Patent No.: US 8,882,477 B2
(45) Date of Patent: Nov. 11, 2014

(54) MAGNETICALLY LEVITATED AND DRIVEN BLOOD PUMP AND METHOD FOR USING THE SAME

(71) Applicant: CircuLite, Inc., Saddle Brook, NJ (US)

(72) Inventors: Bryan Patrick Fritz, IV, Madison, NJ (US); Martin David Simon, Los Angeles, CA (US)

(73) Assignee: CircuLite, Inc., Teaneck, NJ (US)

( * ) Notice: Subject to any disclaimer, the term of this patent is extended or adjusted under 35 U.S.C. 154(b) by 7 days.

(21) Appl. No.: 13/827,645

(22) Filed: Mar. 14, 2013

(65) Prior Publication Data

US 2014/0275723 A1    Sep. 18, 2014

(51) Int. Cl.
| F04B 17/00 | (2006.01) |
| F04B 35/00 | (2006.01) |
| F04B 35/04 | (2006.01) |
| A61M 1/10 | (2006.01) |
| A61M 1/12 | (2006.01) |
| F16C 32/04 | (2006.01) |

(52) U.S. Cl.
CPC ........... *A61M 1/1015* (2014.02); *A61M 1/1008* (2014.02); *A61M 1/1086* (2013.01); *A61M 1/122* (2014.02); *F16C 32/0448* (2013.01); *F16C 2316/18* (2013.01); *A61M 1/101* (2013.01)
USPC ....... 417/423.12; 600/16; 623/3.11; 623/3.19

(58) Field of Classification Search
USPC .......................................................... 600/16
See application file for complete search history.

(56) References Cited

U.S. PATENT DOCUMENTS

| 4,779,614 | A | 10/1988 | Moise |
| 6,201,329 | B1 | 3/2001 | Chen |
| 6,244,835 | B1 | 6/2001 | Antaki et al. |
| 6,302,661 | B1 | 10/2001 | Khanwilkar et al. |
| 2003/0193252 | A1 | 10/2003 | Locke |
| 2008/0240947 | A1 | 10/2008 | Allaire et al. |

OTHER PUBLICATIONS

European Patent Office, International Search Report and Written Opinion in PCT Application Serial No. PCT/US2014/021622, Jul. 7, 2014.

*Primary Examiner* — Carl H Layno
*Assistant Examiner* — Jon Eric C Morales
(74) *Attorney, Agent, or Firm* — Wood, Herron & Evans, L.L.P.

(57) ABSTRACT

A device for pumping blood, includes a housing having a distal end adapted to be coupled to a catheter, a proximal end having an outlet, and a tubular body extending between the distal and proximal ends along an axis. A rotor is rotatably disposed within the housing. A first magnetic bearing is operative to levitate the rotor along the axis within the housing. A second magnetic bearing controls a rotational frequency of the rotor. A third magnetic bearing controls a radial position of the rotor.

24 Claims, 7 Drawing Sheets

MAGNETICALLY LEVITATED AND DRIVEN BLOOD PUMP AND METHOD FOR USING THE SAME

TECHNICAL FIELD

The present invention relates generally to blood pumps and, more specifically, to blood pumps having magnetically levitated and driven rotors.

BACKGROUND

The human heart is the muscle that is responsible for pumping blood throughout the vascular network. Veins are vessels that carry blood toward the heart while arteries carry blood away from the heart. The human heart consists of two atrial chambers and two ventricular chambers. Atrial chambers receive blood from the body and the ventricular chambers, which include larger muscular walls, pump blood from the heart. A septum separates the left and the right sides of the heart. Movement of the blood is as follows: blood enters the right atrium from either the superior or inferior vena cava and moves into the right ventricle. From the right ventricle, blood is pumped to the lungs via pulmonary arteries to become oxygenated. Once the blood has been oxygenated, the blood returns to the heart by entering the left atrium, via the pulmonary veins, and into the left ventricle. Finally, the blood is pumped from the left ventricle into the aorta and the vascular network.

For the vast majority of the population, the events associated with the movement of blood happen without circumstance. However, for many people the heart fails to provide adequate pumping capabilities. These heart failures may include congestive heart failure (commonly referred to as heart disease), which is a condition that results in any structural or functional cardiac disorder that impairs the ability of the heart to fill with or pump blood throughout the body. Presently, there is no known cure for heart disease and long-term treatment is limited to a heart transplant. With only a little over 2,000 patients receiving a heart transplant each year, and over 16,600 more on the waiting list for a heart, there is a persisting need for a cure or at the minimum a means of improving the quality of life of those patients on the waiting list.

One such means of bridging the time gap while awaiting a transplant is a circulatory assist system. Circulatory assist systems may also be utilized as a destination therapy for individuals not eligible for a heart transplant. These systems, originally envisioned over thirty years ago, provide assistance to the heart by way of a mechanical pump. In this way, blood is circulated throughout the vascular network despite the diseased heart tissue. Traditionally, these circulatory assist systems include an implantable or extracorporeal pump, a controller (internal or external), and inflow and outflow tubes connecting the pump to the heart and the vascular network. Food and Drug Administration (FDA) approved circulatory assist systems can partially relieve symptoms of breathlessness and fatigue associated with severe heart failure and drastically improve quality of life.

The wait time for receiving a heart transplant may be substantial. Therefore, circulatory assist systems, and particular the pumps driving them, must be designed for longevity. Furthermore, it is desirable to provide an ideal and advantageous flow of blood therethrough without damaging the blood. There is therefore a need in the art for a pump and a circulatory assist system which experiences low amounts of inter-component friction during operation and causes less damage to blood than other pumps known in the art.

SUMMARY

In one embodiment, a device for pumping blood is provided and comprises a housing having a distal end adapted to be coupled to a catheter, a proximal end having an outlet, and a tubular body extending between said first distal and proximal ends along an axis. The device further comprises a rotor rotatably disposed within the housing, a first magnetic bearing operative to levitate the rotor along the axis within the housing, and a second magnetic bearing controlling a radial position of the rotor, and a third magnetic bearing controlling a radial position of the rotor.

In another embodiment, a device for pumping blood is provide and comprises a housing having a distal end adapted to be coupled to a catheter, a proximal end having an outlet, and a tubular body extending between the distal and proximal ends along an axis. The device further comprises a rotor rotatably disposed within the housing and a first magnetic bearing further comprising first and second permanent magnets and operative to levitate the rotor to an axial position within the housing. A second magnetic bearing is included and further comprises a plurality of vertically arranged pairs of electromagnetic coils and a pole structure coupled to the rotor. The second magnetic bearing is configured to change or maintain a rotational frequency of the rotor. A third magnetic bearing is provided and further comprises the plurality of vertically arranged pairs of electromagnetic coils and the first permanent magnet. The third magnetic bearing is configured to change or maintain a radial position of the rotor. The device further comprises a Hall Effect sensor sensing the radial position and rotational frequency of the rotor and a controller operably coupled to the Hall effect sensor and configured to communicate with the coils to change or maintain the radial position and rotational frequency of the rotor.

A method of operating a rotor of a blood pump is provided and comprises levitating the rotor within a tubular body of the blood pump using a first magnetic bearing, rotating the rotor about an axis within the tubular body using a second magnetic bearing, and maintaining the radial position of the rotor relative to the axis using the third magnetic bearing.

An alternative method of operating a rotor of a blood pump is provided and comprises levitating the rotor within a tubular body of the blood pump using a first magnetic bearing, the first magnetic bearing comprising a first permanent magnet and a second permanent magnet, the second permanent magnet operatively coupled with the rotor. The method further comprises commencing rotation of the rotor within the tubular body using a second magnetic bearing. The second magnetic bearing further comprises a plurality of vertically arranged pairs of coils circumferentially disposed around the housing and a pole structure coupled to the rotor. A current is sent to at least one of the pairs the coils, thereby magnetizing the coil in a first pole direction and urging an oppositely magnetized portion of the pole structure towards the coil. The method further comprises sensing a rotational frequency and a radial position of the rotor. When a sensed rotational frequency is below a threshold level, the method further comprises sending a current to at least a portion of the pairs of coils, thereby further rotating the rotor. When the radial position of the rotor deviates from a threshold position about the axis, sending a current to a pair of coils, thereby urging the rotor towards the axis.

DETAILED DESCRIPTION OF THE DRAWINGS

Figure 1:
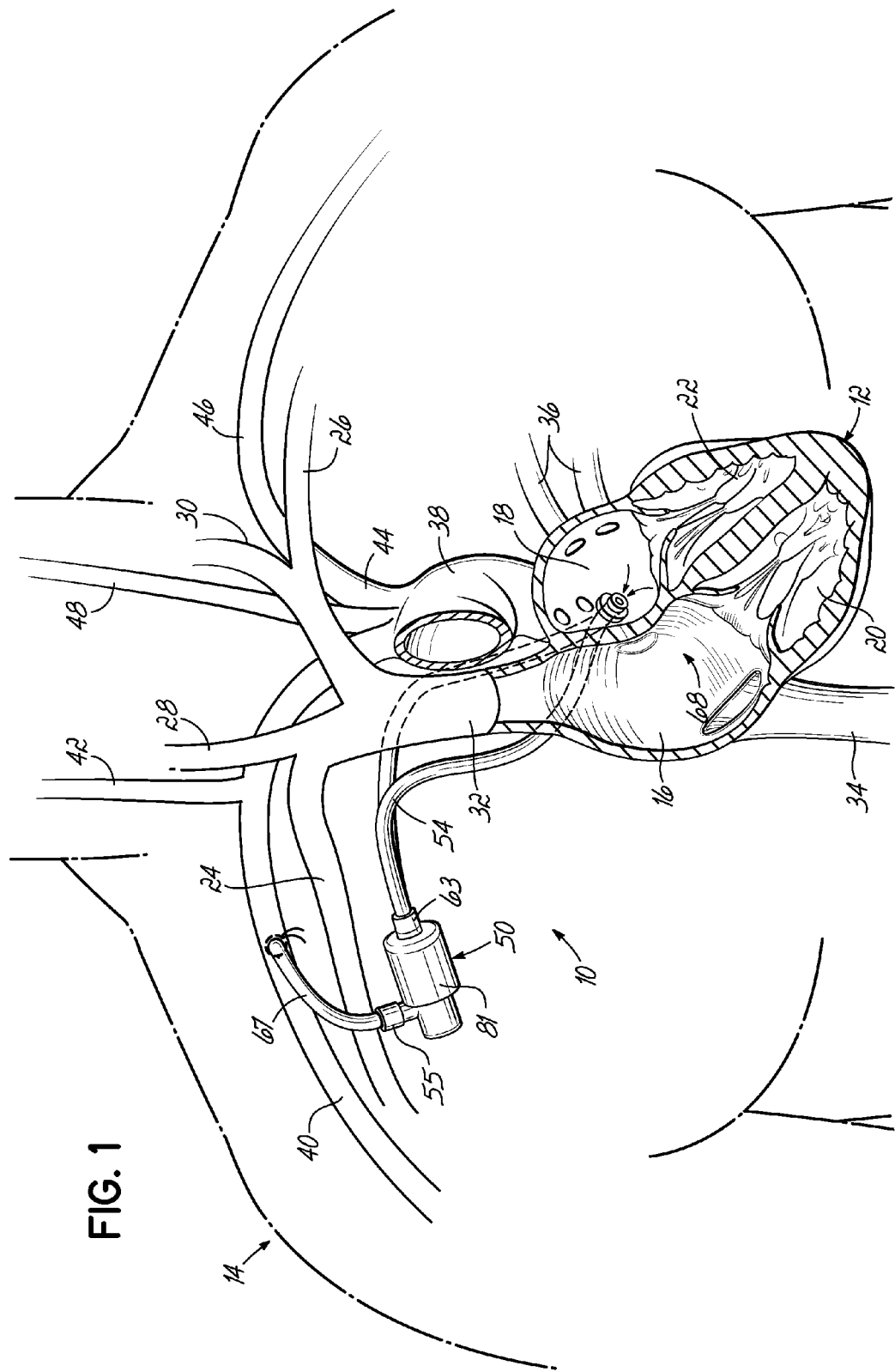
FIG. 1 is a diagrammatic view of an exemplary method of accessing a cavity of the heart.

Turning now to the figures, and in particular to FIG. 1, an implanted circulatory assist system 10 is shown within a chest cavity of a patient 14 with the heart 12 shown in cross-section. For illustrative purposes, certain anatomy is shown, including a right atrium 16, a left atrium 18, a right ventricle 20, and a left ventricle 22. Blood from the left and right subclavian veins 24, 26 and the left and right jugular veins 28, 30 enters the right atrium 16 through the superior vena cava 32 while blood from the lower parts of the body enters the right atrium 16 through the inferior vena cava 34. The blood is pumped from the right atrium 16, to the right ventricle 20, and to the lungs (not shown) to be oxygenated. Blood returning from the lungs enters the left atrium 18 via pulmonary veins and is then pumped into the left ventricle 22. Blood leaving the left ventricle 22 enters the aorta 38 and flows into the left subclavian artery 40, the left common carotid 42, and the brachiocephalic trunk 44 including the right subclavian artery 46 and the right common carotid 48.

With respect to the implanted circulatory assist system 10, two cannulae extend between the vascular network and a pump 50, which may be any implantable or extracorporeal pump that may be radially- and/or axially-driven. Those skilled in this art, however, recognize that other types of pumps may be used in other embodiments but may include pumps such as those described in U.S. patent application Ser. No. 11/627,444, published as 2007/0197854, which is incorporated herein by reference in its entirety.

Figure 2:
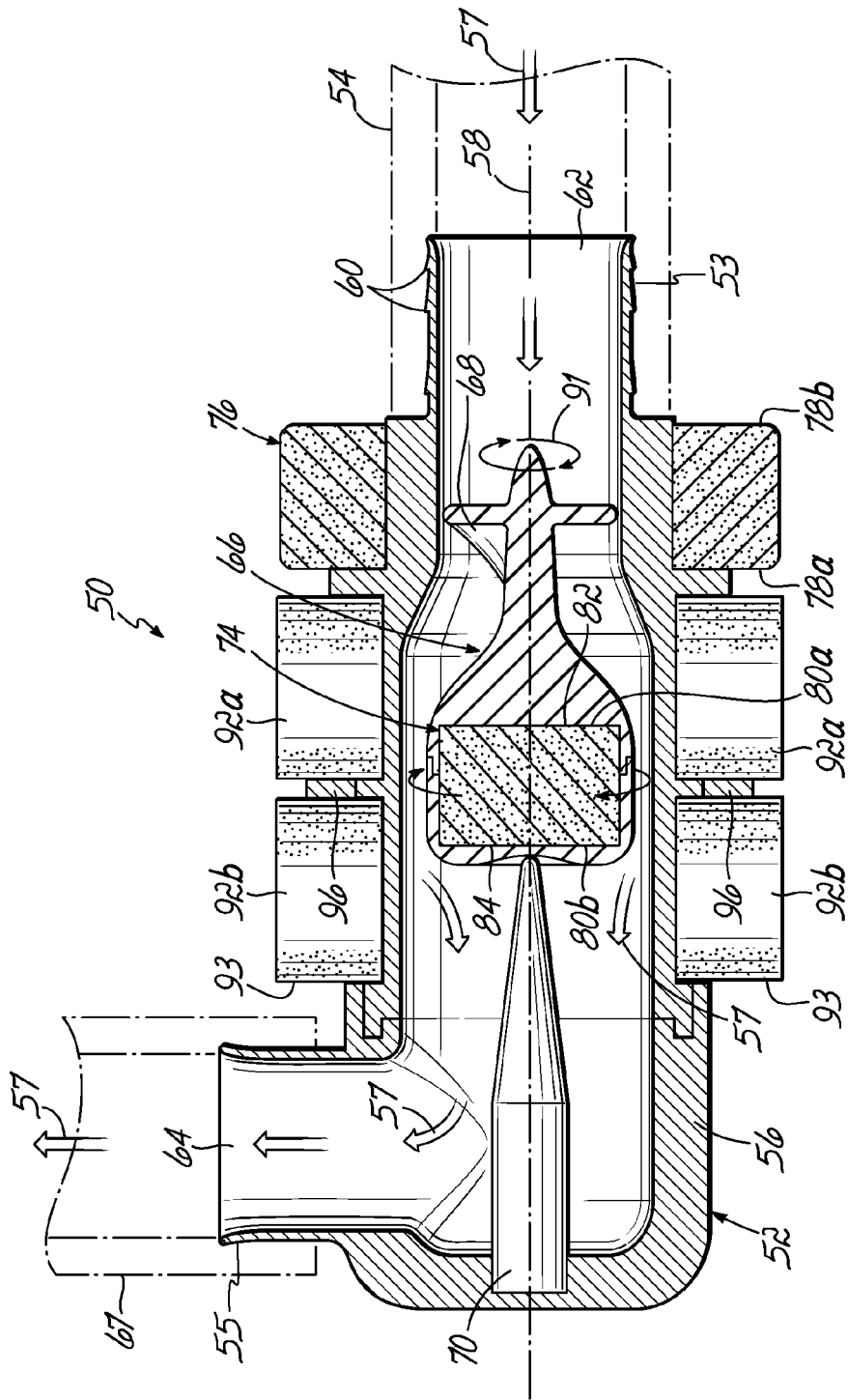
FIG. 2 is a side view in partial cross-section of one embodiment of a blood pump as described herein.

FIG. 2 illustrates the pump 50 in cross-section. In particular the pump 50 includes an elongate pump housing 52 having a first end 53 coupled to a transition portion of the catheter (shown in hidden lines) and a tubular body 56 extending from the first end 53 along a longitudinal axis 58 of the pump housing 52. The first end 53 may be secured to the transition portion by rigid barbs 60, adhesive, or any other coupling technique. In one embodiment of the present invention, the tubular body 56 is defined by a pump inlet 62 at the first end 53 and a pump outlet 64 at the second end 55. There is a shroud 81 (FIG. 5) encasing at least a portion of the housing 52 and the magnetic components, as disclosed below. Blood flows in the inlet 62 at the first end 53 in the direction of arrows 57 and out of the outlet 64 at second end 55.

Various components of a blood pump 50 are housed within the pump housing 52 to draw blood from the catheter 54 into the tubular body 56. For example, the blood pump 50 may comprise an impeller 66 and associated impeller blades 68 positioned within the tubular body 56. It will be appreciated that the impeller 66 is only schematically illustrated and may take many forms, including a form as generally shown herein. The pump 50 may further include a support pin 70 to maintain the axial position therein of the impeller 66 prior to levitation.

Notably, as disclosed herein, "impeller" and "rotor" are used interchangeably and are meant to refer to reference number 66.

The impeller 66 further includes a rotor magnet 74 having dimensions suitable such that the impeller 66 may reside and rotate freely within the tubular body 56. The rotor magnet 74 is a dipole configured to be levitated within the tubular body 56. In one exemplary embodiment of the present invention, the rotor magnet 74 may be 6 mm in diameter and 3 mm in height for pumps configured to operate as left ventricular assist pumps; yet, it would be readily appreciated that the size of the rotor magnet 74 may vary and depend, at least in part, on the size of the impeller blades 68 and a desired blood flow rate. The impeller blades 68 are configured to prevent damage to the blood traveling through the tubular body 52.

In one embodiment, the levitation of the impeller 66 is accomplished due to a first magnetic bearing. More specifically, the first magnetic bearing includes the ring magnet 76 and the rotor magnet 74 which, in one embodiment, are both permanent magnets. The ring magnet 76 and the rotor magnet 74 are configured such that the oppositely magnetized sides are facing one another. For example, the north pole side 78a of the rotor magnet 74 faces the south pole side 80a of the ring magnet 76. Moreover, the configuration of the magnets 74, 76 may be chosen such that the interaction between the magnets 74, 76 creates an asymmetrical potential energy well, as shown by the magnetic field diagram in FIG. 3. The radial potential is shown in the FIG. 3 as a generally hemispherical shape 73. The asymmetric potential well is created due to the presence of ring magnet 76 opposing only one side the rotor magnet 74. The potential well creates stability in the axial direction. Because the depth of the well correlates with the amount of instability in the radial direction, the well may be designed in order to provide the least radial instability while also providing a proper amount of axial stability. In one embodiment, the rotor magnet 74 includes a 6 mm diameter and a 3 mm height. The ring magnet 76 includes an inner diameter of 8 mm, an outer diameter of 14 mm and a height of 3 mm. The potential well creates interactions between the respective magnetic fields of each magnet 74, 76, which results in levitation of the rotor magnet 74 relative to the ring magnet 76. Moreover, the asymmetric potential well may be configured to provide a levitation force approximately equal and opposite to the fluid forces resulting from the blood flow and pumping action (i.e., rotation of the impeller 66). This provides several benefits, including simplification of design. In order to vary the levitation force and the size of the asymmetric potential well, the relative sizes of the rotor and ring magnets 74, 76 may be altered.

Figure 4:
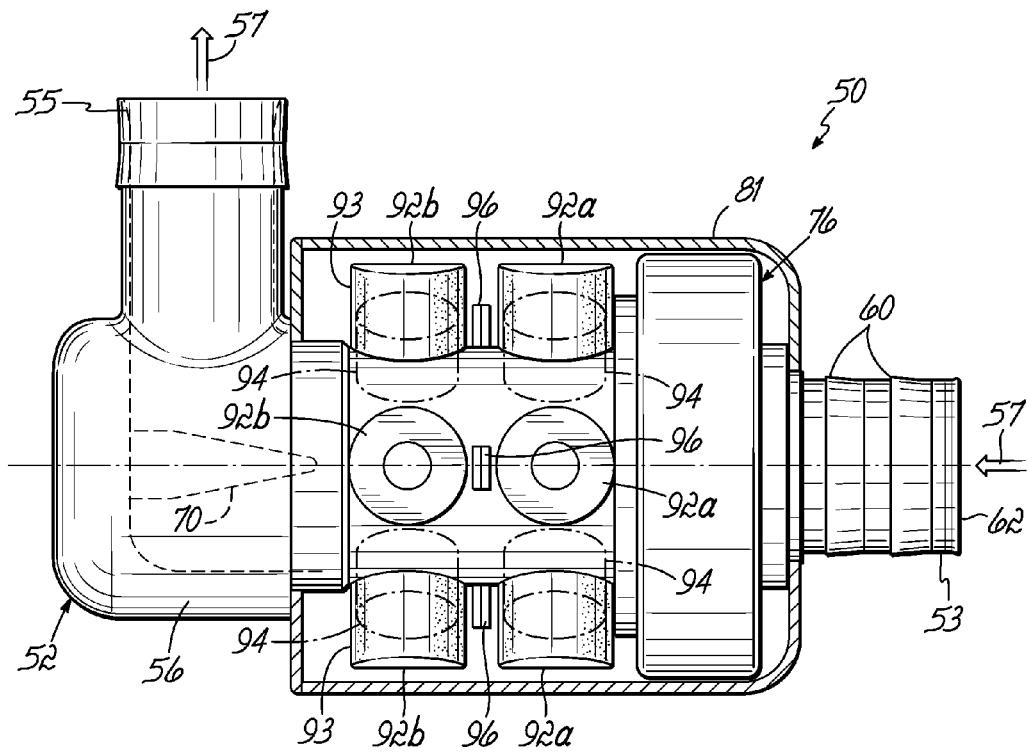
FIG. 4 is a side view of the pump of FIG. 2 including supplementary electromagnetic coils.
Figure 5:
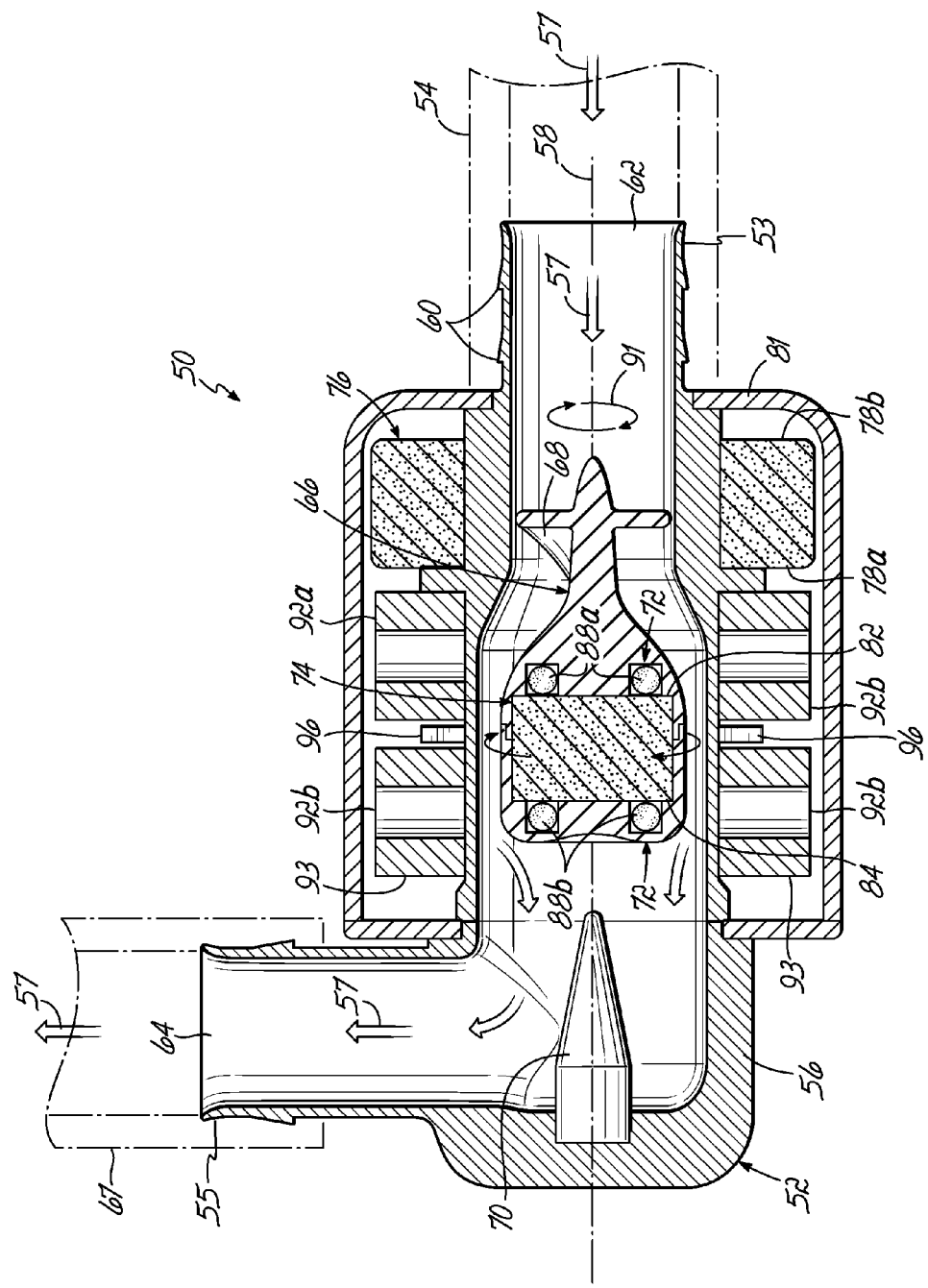
FIG. 5 is a side cross-sectional view of the pump of FIG. 2.

Therefore, while the impeller 66 may be levitated by the potential well (FIG. 3), the rotor magnet 74 and thus the impeller 66 may inherently be unstable in the radial direction unless the rotor magnet 74 is rotating. Even then, the rotor magnet 74 may be unstable such that the rotor magnet 74, and thus the impeller 66, may tilt or move radially away from axis 58. The rotation of the rotor magnet 74 is operative to provide stability in the radial direction of the rotor magnet 74 and thus the impeller 66. The rotation of rotor magnet 74 is effectuated at least in part by a second magnetic bearing, which is discussed in more detail below. The embodiment shown in FIGS. 2, 4 and 5 shows the ring magnet 76 being situated distally relative to the rotor magnet 74. However, in other embodiments, it may be appreciated that the ring magnet 74 may be situated proximally relative to the rotor magnet 74 and still provide the potential well that is operative to levitate the rotor magnet 74, and thus the impeller 66, within the tubular body 56.

Alternatively, the levitation of the impeller 66 may be accomplished by use of alternative materials, such as diamagnets. As understood by a person skilled in the art, diamagnets are non-ferrous materials that when placed in a magnetic field, exhibit a repulsion force towards the magnetic source. Therefore, in a preferred embodiment, at least one of the rotor magnet 74 or the ring magnet 76 may comprise a diamagnet. Preferably, in that embodiment, the rotor magnet 74 is a diamagnet while the ring magnet 76 is a permanent magnet as disclosed herein.

The magnetic portion or pole structure 72 may further include two or more poles on both top and bottom edges 82, 84 of the rotor magnet 74. In one embodiment, the top and bottom edges 82, 84 each include a four pole structure 72, which may be constructed by magnetic coding of the edges of the rotor magnet 74 by methods such as those taught in U.S. Pat. No. 7,800,471, issued on Sep. 21, 2010, and entitled FIELD EMISSION SYSTEM AND METHOD, such magnetic coding services commercially-available from Correlated Magnetics Research, LLC (New Hope, Ala.). Alternatively, as shown in FIGS. 5 and 6A-C, the structure may include physically embedded miniature sub-magnets, or pill magnets 88a, 88b within the impeller 66. In any event, the pole structure is positioned such that the resultant magnetic field is oriented to oppose the magnetic field of the rotor magnet 74 or radially outwardly from the rotor magnet 74. The pole structure 72 may be provided to function as one part of a magnetic bearing that interact with the coils 92 as described herein. The pole structure 72 may alternatively include a magnet including several poles, such as a quadropole magnet, which may then be attached or coupled to the rotor magnet such that it is also embedded in the impeller 66.

Figure 6A:
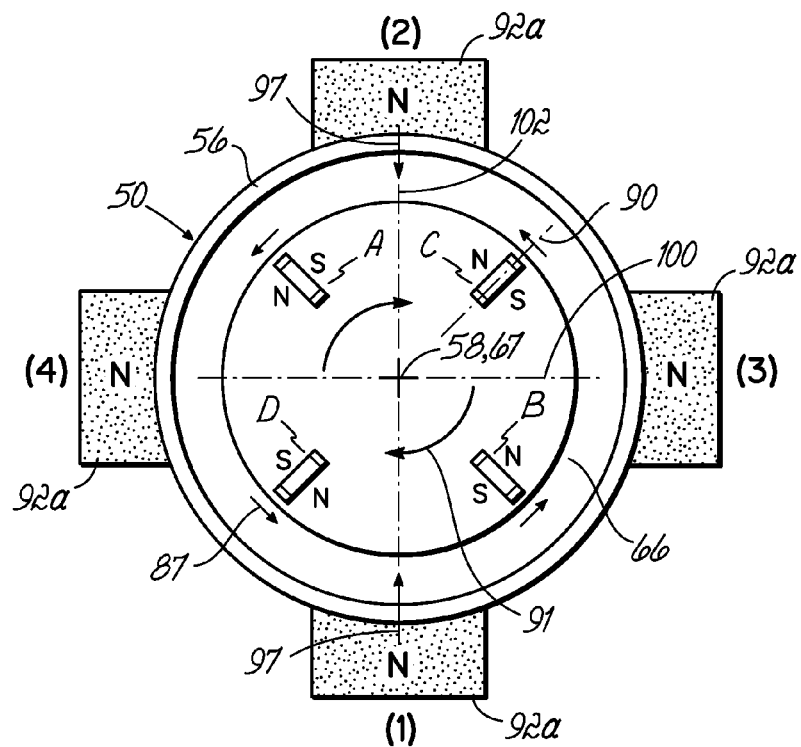
FIGS. 6A through 6C are top views of a schematic representation of the device of claim 1 showing the functionality of the coils.
Figure 6B:
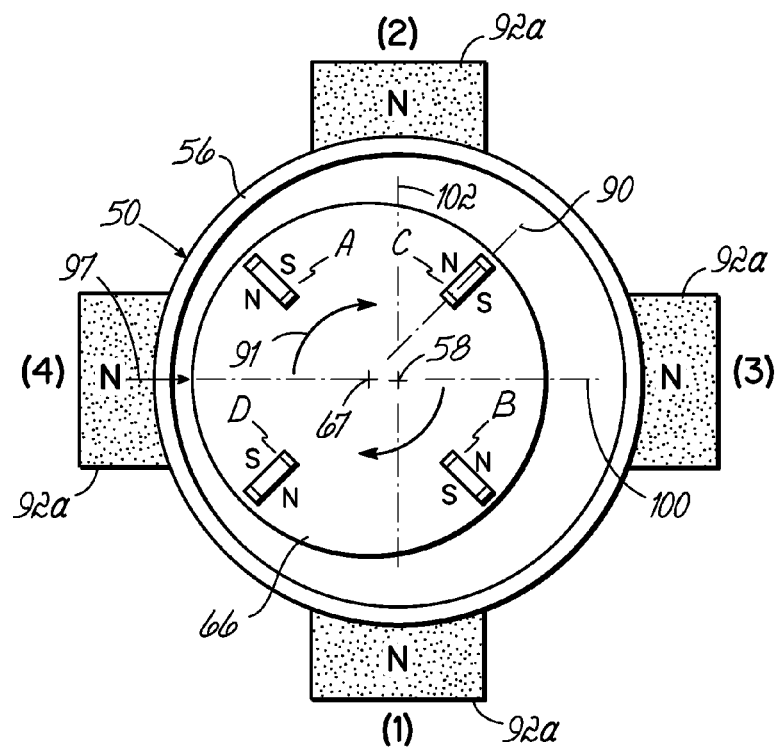
Figure 6C:
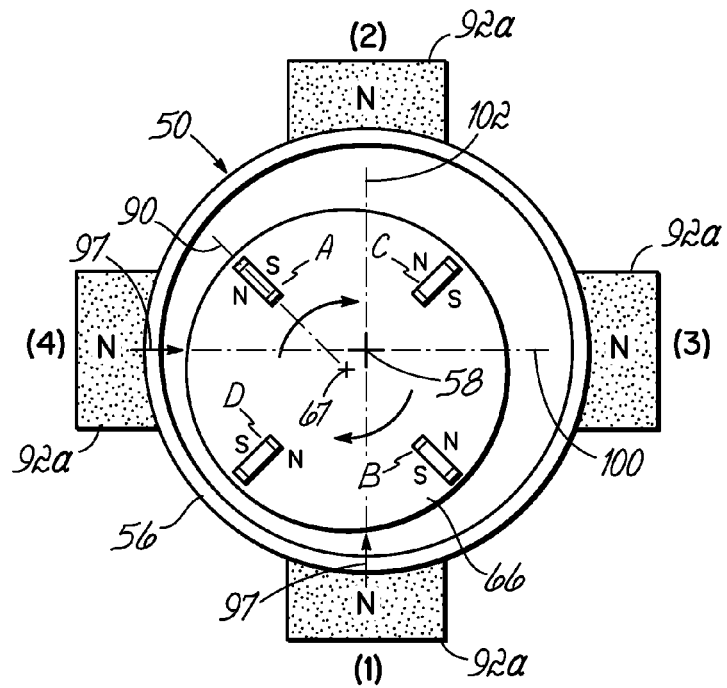

One embodiment of the pole structure 72 is shown in FIGS. 5 and 6A-C. In the embodiment shown in FIGS. 5 and 6A-C, there are four sub-magnets, or pill magnets 88a, 88b on the top and the bottom 82, 84 of the rotor magnet 74, respectively. In alternative embodiments, however, there may be more pill magnets 88a, 88b on each of the top and the bottom 82, 84 such as six or eight. Alternatively, there may be less, such as two. Preferably, as shown in FIG. 5, the pill magnets 88a, 88b are embedded in the impeller 66. The pill magnets 88a, 88b are preferably cylindrically shaped and axially magnetized (FIGS. 6A-C). In another embodiment, the pill magnets 88a, 88b may be diametrically magnetized. In yet another embodiment, the pill magnets may be a shape other than a cylinder, such as a triangular or rectangular prism, or another shape. The pill magnets 88a, 88b may be situated such that the direction of magnetization 87 of the pill magnets 88a, 88b is tangent to the direction 91 of rotation of the impeller 66. However, depending on the shape and configuration, the direction of magnetization 87 of the pill magnets 88a, 88b may be different.

The pump 50 further includes a plurality of electromagnetic coils 92a, 92b disposed on or adjacent the housing 52. In a preferred embodiment, as shown in FIGS. 2, 4 and 5, the pump 50 includes four vertically arranged, equally circumferentially spaced pairs of electromagnetic coils 92a, 92b. Each pair of coils 92a, 92b includes upper and lower coils 92a, 92b, respectively. Each vertically arranged pair of coils 92a, 92b is in series and counterwound such that, for example, upper coil 92a of a pair is wound in a counterclockwise direction and the lower coil 92b is wound in a clockwise direction. However, in an alternative embodiment, the coils may be wound in alternative configurations. For example, coils 92a, 92b could also be wound the same direction and wired so that the current flows in one direction through the top and the opposite direction in the bottom, thereby producing opposite magnetic fields. The coils 92a, 92b are preferably encased with housings 93 comprising a non-magnetic material as not to interfere with the functionality of the pump 50. In an alternative embodiment, however, there may be less than four vertically arranged pairs of coils 92a, 92b. For example, there may be more than four pairs, or less than four pairs. There may be supplemental coils 94, as shown in FIG. 4.

In one embodiment, the coils 92a, 92b may comprise an iron core (not shown) to strengthen the magnetic field emitted by the coils 92a, 92b. The coils 92a, 92b and the pole structure 72, such as the pill magnets 88a, 88b, may be the second magnetic bearing that effectuates the rotation of the rotor magnet 74, and thus the impeller 66. The rotation of the rotor magnet 74 and impeller 66 provides for axial stability of the levitated rotor magnet 74, and thus the impeller 66. The rotation of the rotor magnet 74 and thus the impeller 66 are described in more detail below. The device further includes a third magnetic bearing which is configured to control a radial position of the rotor 66. As described in further detail below, the third magnetic bearing includes the rotor magnet 74 and the coils 92, 92b.

Preferably, the coils 92a, 92b are wound from a material, such as copper, capable of conducting electricity such that a current will travel through the coils 92a, 92b and energize the coils 92a, 92b, thereby magnetizing the coils 92a, 92b. Coils 92a, 92b receiving current and thereby being magnetized may be referred to herein as "energized" or "magnetized." The direction of the current flow through the coils 92a, 92b determines the direction of magnetization, i.e., whether the coils will be magnetized as a south pole or a north pole. For example, in a preferred embodiment, the upper coils 92a of a pair are wound in the clockwise direction such that when the upper coils 92a are energized, the upper coils 92a are magnetized in the north pole direction, as indicated by "N" on FIG. 6A-C. Similarly, in a preferred embodiment, the lower coils 92b are wound in the counterclockwise direction such that when the lower coil 92b is energized, the lower coils 92b are magnetized in the south pole direction (not shown).

Because each vertically arranged pair of coils 92a, 92b in a preferred embodiment are in series, when the coils 92a, 92b are energized when receiving a current, the upper coils 92a are magnetized in the north pole direction and the lower coils 92b are magnetized in the south pole direction. However, as will be recognized by persons skilled in the art, the current may be sent in different directions to the upper and lower coils 92a, 92b, resulting in different magnetization directions of each pair of coils 92a, 92b. Ultimately, changing the direction of the current directed into the coils 92a, 92b changes whether a coil 92a, 92b is magnetized in the north or south pole direction.

In one embodiment, each coil 92a, 92b comprises a #42 AWG copper wire with approximately 750 turns per coil 92a, 92b, made by Precision Ecowind, Inc. of North Fort Myers, Fla. With this diameter and amount of turns, the resistance per coil 92a, 92b is approximately 50Ω. However, the coil 92 may comprise a different diameter, material, and amount of turns, depending on the desired characteristics of the coils 92a, 92b, which ultimately depend on the desired characteristics of the blood pump 50 (i.e., desired rotational frequency of the blood pump 50 or required force to radially align the impeller 66). The current sent to the coils 92a, 92b to thereby energize the coils 92a, 92b may be between approximately 0 mA and 200 mA and depends on the characteristics of the coils 92a, 92b described herein as well as the desired characteristics of the blood pump 50.

FIGS. 6A through C show an embodiment of the pump 50 showing the upper coils 92a and upper pill magnets 88a of the pump 50. A second magnetic bearing is utilized in order to begin rotation of the impeller 66. A current may be sent to diametrically opposed pairs of coils 92a, 92b simultaneously by the controller (FIG. 8), thereby magnetizing the pairs of coils 92a, 92b in a certain direction. The magnetized coils 92a, 92b then either attract or repel one or more of the pill magnets 88a, 88b, depending on the rotational location of each of the pill magnets 88a, 88b relative to the magnetized coils 92a, 92b. In order to clarify the functionality of the coils 92a, 92b during the operation of the device, the specific upper coils 92a are labeled 1, 2, 3 and 4, while the specific upper pill magnets 88a are labeled A, B, C, and D in FIG. 6A-C. Preferably, to begin rotation, coils 1 and 2 are energized and are thereby magnetized in the north direction. The south poles of pill magnets B, A thereby become attracted to, and are urged towards, coils 1 and 2, respectively. Because of the diametrically opposed configuration of the energized coils 1, 2, the attractive forces are essentially balanced. Furthermore, because the pill magnets B, A are embedded in the impeller 66, and the rotation of pill magnets B, A causes the impeller 66 to begin to rotate in the clockwise direction 91. The interaction between the lower coils 92b and lower pill magnets 88b would correspond to the interaction between the upper coils 92a and upper pill magnets 92a. For example, in a preferred embodiment as disclosed above, the lower coils 92b are magnetized in an opposite pole direction of the upper coils 92a. Therefore, in order to attract or repel the lower pill magnets 88b as discussed herein, the configuration of the lower pill magnets 88b may need to be reversed such that the north poles and south poles are facing opposite directions as shown in FIGS. 6A-C.

The Hall Effect sensors 96 sense the magnetic fields of the pole structure 72 (such as the pill magnets 88a, 88b) as well as the rotor magnet 74. With this magnetic field information, the Hall Effect sensors 96 may sense the radial and axial positions of the pill magnets 88a, 88b, as well as the rotational frequency of the pill magnets 88a, 88b, and thus the impeller 66. The Hall Effect sensors 96 essentially determine whether the rotation frequency is at, below, or above a threshold rotational frequency. Further, the Hall Effect sensors 96 communicate with the controller 98 (FIG. 8) to selectively energize certain coils 92a, 92b to rotate the impeller 66. Preferably, the Hall Effect sensors 96 use the rotational frequency and position information to communicate with the controller 98 as to which coils 92a, 92b to energize and/or de-energize. Using the upper pill magnets and coils 88a, 92a by way of example, as a pill magnet 88a approaches a coil 92a, the controller 98 may de-energize the coil 92a until the pill magnet 88a rotates past the coil 92a. More specifically, in FIG. 6B, pill magnets B, A have rotated past de-energized coils 3 and 4, respectively. The north poles of pill magnets B, A are facing the coils 3, 4, respectively. After the Hall Effect sensor 96 has sensed that the pill magnets B, A have rotated past coils 3 and 4, the sensor 96 communicates with the controller 98 regarding the position of pill magnets B and A. The controller 98 then energizes coils 3, 4 in the north direction and pill magnets B, A are repelled away from coils 3, 4. Because of the diametrically opposed configuration of the energized coils 3, 4, the repelling forces are essentially balanced and the impeller 66 continues to rotate about the axis 58. The upper coils 92a as shown in FIGS. 6A-C may be magnetized in the north direction. However, in alternative embodiments, the selectively energized coils 3, 4 may be magnetized in the south direction. Therefore, in that alternative embodiment, the configuration of the pill magnets B, A may need to be altered in order for the repelling and/or attractive forces to occur as coils 3, 4 are selectively energized. The orientation and configuration of the pill magnets 88a, 88b relative to the coils 92a, b may be determined by the desired rotational direction.

Moreover, it may be appreciated that in embodiments with an alternative configuration or different amount of coils 92a, 92b and/or pill magnets 88a, 88b, for example, the rotational frequency may be altered or maintained in similar manner such that the forces on the rotor 66 are balanced, thus causing rotation of the rotor 66. For example, as discussed above, the embodiment as shown in FIGS. 6A-C includes four vertically arranged pairs of coils 92a, 92b. One manner of maintaining or altering the rotation of the rotor 66 is, as discussed, sending a current to diametrically opposed pairs of coils 92a, 92b such that the magnetic forces from each coil 92a, 92b may be balanced along the axes 100, 102 and thus rotation of the rotor 66 occurs. However, which coils 92a, 92b to energize in order to provide balanced magnetic forces upon the rotor or impeller 66 depends on the configuration and number of the coils 92a, 92b as well as the configuration of the pole structure 72, such as the number of pill magnets 88a, 88b. In an alternative embodiment, rather than including a pole structure 72, such as pill magnets 88a, 88b, for rotation, the coils 92a, 92b may interact with the dipole moment of the impeller magnet 74 in order to effect rotation of the rotor magnet 74, and thus the rotor 66.

The Hall Effect sensors 96 also use the magnetic field information of the pole structure 72 (such as the pill magnets 88a, 88b) and the rotor magnet 74, to sense the radial position of the impeller 66, relative to the axis 58 of the pump 50. To control radial position of the rotor 66, a third magnetic bearing is utilized. In a similar manner as with respect to the rotational frequency discussed hereinabove, the Hall Effect sensors 96 communicate with the controller 98 to selectively energize certain coils 92 to alter the radial position of the rotor magnet 74, and thus the impeller 66, relative to the axis 58. As described herein, "off-axis" may be used to characterize the position or movement of the impeller 66 where the impeller 66 is positioned radially away from the axis 58 along axes 100 and 102, which are transverse to the axis 58 of the blood pump 50. Moreover, axes 100, 102 are transverse to one another. Which coils 92a, 92b are energized depends on the off-axis position of the impeller 66.

Figure 3:
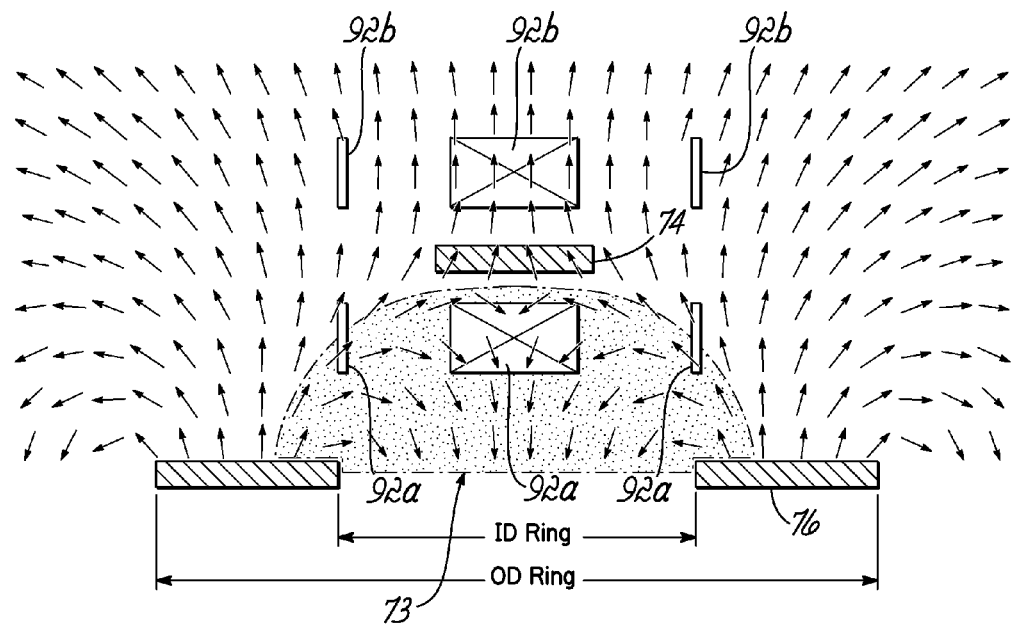
FIG. 3 is a diagram of magnetic fields associated with the pump of FIG. 2.

As shown in FIG. 6B, the radial position of the impeller 66 is characterized by an off-axis position along a single axis 100, or a generally left direction, due to the radial instability caused by the asymmetric potential well (FIG. 3). The Hall Effect sensors 96 may sense that the rotor 66 is not in a threshold position, the threshold position being characterized by the center axis 67 of the rotor 66 being essentially aligned with axis 58. Therefore, it may be desirable to alter the position of the impeller 66 in the generally right direction along axis 100. To accomplish this positional alteration, the Hall Effect sensors 96 communicate with the controller 98 to energize coil 4 in the north direction, as indicated by arrows 97. Because each pair of coils 92 is wired in series and counterwound, the lower coil 92b below coil 4 would be magnetized in the south direction. The rotor magnet 74, as discussed above, is oriented such that the north pole side 80a is essentially adjacent the upper coils 92a (i.e. coil 4), while the south pole side 80b is essentially adjacent the lower coils. The north-direction magnetization of coil 4 thereby repels the north pole side of 80a, while the south-direction magnetization of the lower coil 92b associated with coil 4 repels the south pole side 80b. Therefore, the forces from coil 4 and the associated lower coil 92b are balanced angularly with respect to axis 58. Moreover, energizing the coils generates forces that provide stability in the radial direction. The rotor magnet 74, and thus the impeller 66, are thereby urged towards the axis 88 along axis 100. It may be appreciated that, instead of energizing coil 4 to repel rotor magnet 74 away from coil 4 and towards axis 58 along axis 100, coil 3 may be energized in a direction to attract rotor magnet 74 towards coil 3 (and the associated lower coil 92b), thereby urging the impeller 66 towards the axis 58. Moreover, where extra force may be needed to urge the rotor 66 in the direction of axis 58, coils 3 and 4 may be energized such that coil 3 attracts the impeller towards axis 58 and coil 4 repels the impeller 66 towards axis 58. It may be appreciated that, due to the generally hemispherical shape of the potential well, the impeller magnet 74 may be urged slightly in the axial direction during radial positioning by the coils 92a, 92b.

As shown in FIG. 6C, the radial position of the impeller 66 is characterized by a movement in the left and down directions along axes 100 and 102, respectively, and radially away from the axis 58. Therefore, it may be desired to move the impeller 66 in the up and right directions towards the axis 58. To accomplish this positional alteration, the Hall Effect sensors 96 communicate with the controller 98 to energize adjacent coils 1 and 4 in the north pole direction, as indicated by arrows 97, and the associated lower coils (not shown) in the south pole direction. Similar to the description of FIG. 6B above, magnetizing coils 1 and 4 and the associated lower coils (not shown) thereof urges the rotor magnet towards axis 58 due to the repelling force between the energized coils and the rotor magnet 74.

Altering or maintaining the radial position of the rotor 66 as described herein with respect to FIGS. 6B and 6C also assists in counteracting tilt of the rotor 66. The natural tendency of the south pole side 78a of the rotor magnet 74 is to be attracted to the north pole side 80a of the ring magnet 76. Therefore, as the rotor 66 rotates, the rotor 66 may experience tilt, wherein a center axis 67 of the rotor 66 is angularly displaced relative to the axis 58. The device and method of counteracting off-axis radial movement as described herein is also adapted to counteract tilt. In an alternative embodiment, it may be advantageous to provide additional coils 92a, 92b for alteration and/or maintenance of rotational frequency, radial position and tilt. In one embodiment, for example, the device may be configured to energize one or more coils 92 from one of the upper or lower sets 92a, 92b in order to urge the rotor 66 angularly towards the axis 58.

It is appreciated that the manners, frequency and continuity of energizing the coils 92 and the directions of magnetization resulting therefrom may be altered depending on the number of and configurations of the pill magnets 88a, 88b and coils 92a, 92b. The descriptions hereinabove of altering or maintaining the rotational frequencies and radial positions of the impeller 66, as well as counteracting tilt, are simply examples and are not meant to limit the device and method described herein to only those examples.

Figure 7:
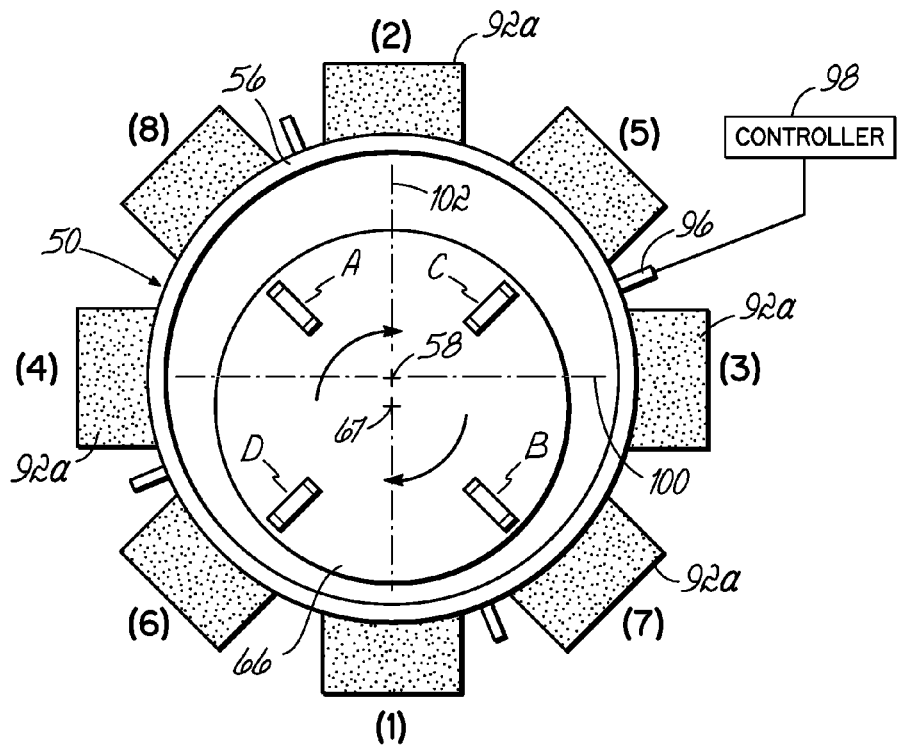
FIG. 7 is a top view of a schematic representation of an alternative embodiment of a device as described herein.

One alternative embodiment is shown in FIG. 7. For example, where there are more than four vertically arranged pairs of coils 92a, 92b, the amount of ways that the coils 92a, 92b may be energized to alter or maintain the rotational frequency, radial position, and tilt is increased. By way of example, in one embodiment, there may be eight pairs of vertically arranged coils 92a, 92b. This embodiment may effectuate the control of rotational frequency, radial position and tilt as described hereinabove. As in previously disclosed embodiments, which coils 92a, 92b are energized depends on the off-axis position of the impeller or rotor 66. For example, as shown in FIG. 7, the impeller 66 has moved off-axis in the downward direction along axis 102. Because of the additional coils, there is an increased amount of ways in which the rotor 66 may be urged towards the axis 58. For example, depending on the positions, and magnetization configuration of the rotor magnet 74, the coils 2, 5 and 8 may be energized and attract, or essentially pull the rotor magnet 74, thus urging the rotor in the direction of the axis 58 along axis 102. Coils 1, 6 and 7 may be concurrently energized such that it provides a magnetic force such that it repels, or pushes, the impeller magnet 74. This repulsive force from coils 1, 6 and 7 may thereby balance the force from coils 2, 5 and 8 directing the rotor along axis 102, thus maintaining the rotor rotating about axis 58. It is appreciated, as disclosed previously, that the lower coils (not shown) associated with coils 1, 2, 5, 6, 7 and 8 may be oppositely magnetized and simultaneously energized with the associated upper coils 1, 2, 5, 6, 7 and 8, thereby preferably balancing the magnetic forces from the coils. Moreover, as previously discussed, the radial alteration and maintenance of the rotor 66 by the coils 92a, 92b also assists in counteracting tilt of the rotor 66. FIGS. 6A-C and 7 are provided as exemplary embodiments. These figures and the disclosure regarding these figures are provided as an example of just a few manners in which the rotational frequency, radial position and tilt may be altered or maintained using the device as disclosed herein. It is appreciated that the amount of coils 92a, 92b, and the pole structure 72, such as the amount pill magnets 88a, 88b, may vary. Furthermore, the size, orientation, position and characteristics of the rotor magnet 74 may be varied. Moreover, the manner in which the coils 92a, 92b are controlled in order to alter or maintain the rotational frequency, radial position and tilt may also vary. It is further appreciated that when varying the amount of coils 92 and the pole structure 72, additional controllers 98 (FIG. 8) and Hall Effect sensors 96 may be required.

Due to the loading on the impeller, it may also be appreciated by persons skilled in the art that the flow of blood through the housing 52 past the impeller, as well as the rotation of the impeller 66, may cause the impeller 66 to oscillate in the axial direction along axis 58. The Hall Effect sensors 96 are configured to detect the oscillation of the impeller 66. One of the embodiments described herein may be configured to counteract oscillation of the impeller 66. On the other hand, additional coils 92a, 92b may be provided in order to counteract the axial oscillation of the impeller 66.

In another alternative embodiment, a blood pump 50 includes a supplemental set of coils 94 (shown in phantom in FIG. 4) circumferentially disposed about the housing 52. Preferably, the supplemental coils 94 comprise four coils 94 equally circumferentially spaced, wherein each secondary coil 94 is offset ninety degrees from an adjacent pairs of vertically arranged coils 92. In the embodiment shown in FIG. 4, the vertically arranged pairs of coils 92a, 92b are utilized for maintaining or altering the radial position of the impeller 66 in the same manner as substantially described herein. The supplemental coils 94 in this embodiment may be utilized for maintaining or altering the rotational frequency of the impeller 66 in the same manner as described substantially herein. Because of the supplemental coils, one or more additional Hall Effect sensors 96 may be required. Alternatively, the vertically arranged pairs of coils 92a, 92b may be utilized for maintaining or altering the rotational frequency of the impeller 66, while the secondary coils 94 may be utilized for maintaining or altering the radial position of the impeller 66.

The rotational frequency of the pill magnets 88a, 88b, and thus the impeller 66, are essentially continuously sensed or monitored by the Hall Effect sensors 96. The Hall Effect sensors 96 essentially continuously communicate with the controller 98 to energize diametrically opposed sets of coils 92*a*, 92*b*, depending on the positions of the pill magnets 88*a*, 88*b*, in order to change the rotational frequency of the impeller 66 or to maintain the rotational frequency of the impeller 66. The required rotational frequency of the impeller 66 depends on certain variables such as the physiological needs of the patient and the dimensions of the impeller 66 and of the blood pump 50, for example. In one embodiment of a blood pump 50 having an inner housing diameter of 5 mm, a rotational frequency of 17,000 to 32,000 revolutions per minute produces a flow of 0.3 to 2.5 LPM at normal physiological pressures as known to those skilled in the art. The configuration of the blood pump of the aforementioned embodiment allows the blood pump 50 to be smaller than the blood pumps known in the art. The smaller size of blood pump 50 provides a less invasive configuration and can lower costs.

More specifically, there is a plurality of Hall Effect sensors 96 circumferentially disposed on the device 50. Preferably, there are at least two Hall Effect sensors 96 equally circumferentially disposed on the device 50. As shown in FIGS. 2, 4 and 5, the device includes four Hall Effect sensors 96, where each Hall Effect sensor 96 is essentially aligned with a vertically arranged pair of coils 92*a*, 92*b*. Each Hall Effect sensor 96 may be used to sense at least one of the rotational frequency and the radial position of the impeller 66. However, in one embodiment, one or more of the Hall Effect sensors 96 may be used to sense only the rotational frequency and another portion of the Hall Effect sensors 96 may be used to sense the radial position of the impeller 66.

Figure 8:
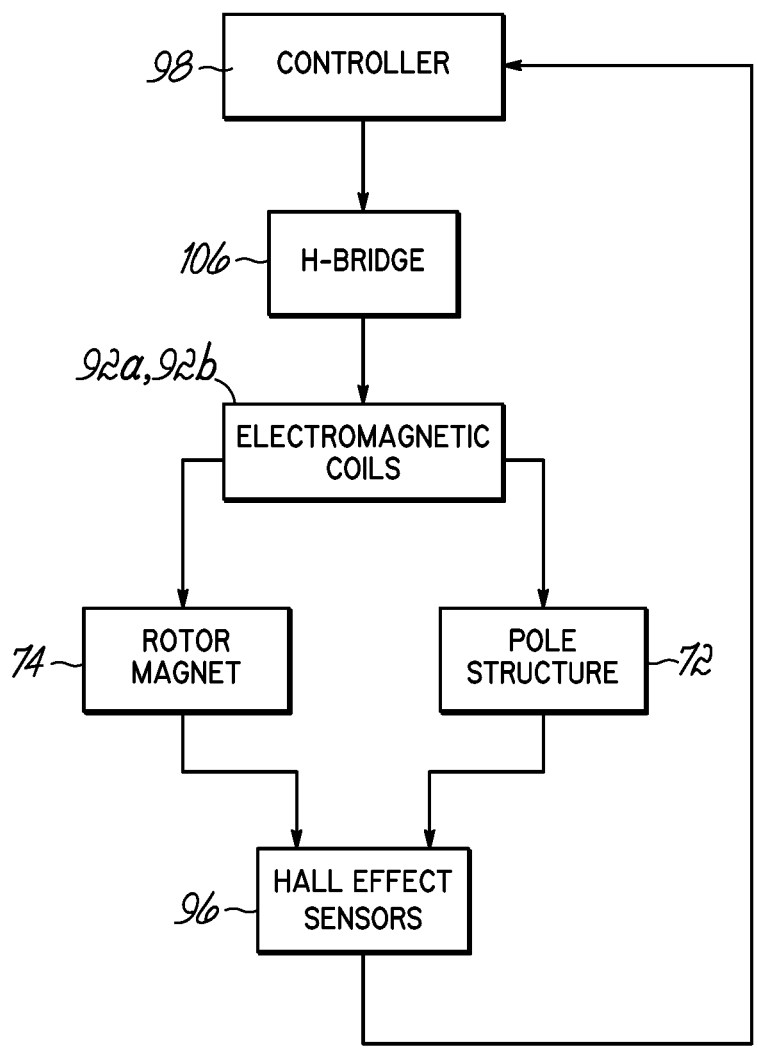
FIG. 8 is a schematic diagram of the controllers, sensors and circuitry of the pump of FIG. 2.

FIG. 8 shows a control loop 104. As disclosed herein, and with reference to FIG. 8, the Hall Effect sensors 96 communicate with at least one controller 98 in order to selectively energize, or send current through, the coils 92. In a preferred embodiment, there is a plurality of controllers 98 communicating with the sensors 96. More preferably, each controller 98 is a proportional-integral-derivative (PID) controller which, based on the information sent it from the Hall Effect sensors 96 based on the magnetic field information, calculates the present, past and future errors. To adjust for the present, past and anticipated future errors (such as off-axis rotation), the PID controllers 96 then selectively energize, or send a current through, one or more coils or pairs of coils 92*a*, 92*b* by way of the H-Bridge 106.

More specifically, the Hall Effect sensors 96 receive the magnetic field information from the rotor magnet 74 and the pole structure 72. With the magnetic field information from the Hall Effect Sensors, the controller 96 is able to determine the position and rotational frequency of the rotor magnet 74 and the pole structure 72, and thus the impeller 66, and compare such with threshold data. The radial position may be sensed in the X and Y positions (FIG. 8), such as along axes 100 and 102 (FIGS. 6A through 6C). The threshold data may also be obtained through observance of the current traveling in the coils 92*a*, 92*b*. In at least one embodiment, it is observed that as the impeller 66 approaches the threshold position, the current passing through the coils reduces. Observing that phenomenon may allow a person skilled in the art to detect the position and rotational frequency of the impeller 166. The threshold data may include a predetermined, desired rotational frequency and radial position. When the rotational frequency and radial position as sensed by the Hall Effect sensors deviate from the predetermined, desired values, the controller sends a signal over the H-Bridge, thereby selectively energizing coils 92*a*, 92*b*.

The coils 92*a*, 92*b* which are energized depends on the desired outcome as described above with respect to at least FIGS. 6A-C, such as altering or maintaining the radial position or rotational frequency of the impeller 66. In one embodiment, there are four PID controllers 98, each being part of a control loop 104 including an H-bridge 106. However, the number of, type, and arrangement of the controllers 98 as described herein is but one possibility of controlling the device 50 as described herein and the disclosure is not meant to be limited to only the embodiments described herein.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A device for pumping blood, comprising:
a housing having a distal end adapted to be coupled to a catheter, a proximal end having an outlet, and a tubular body extending between said first distal and proximal ends along an axis;
a rotor rotatably disposed within the housing;
a first magnetic bearing operative to levitate the rotor along the axis within the housing;
a second magnetic bearing controlling a rotational frequency of the rotor;
a third magnetic bearing controlling a radial position of the rotor;
at least one Hall Effect sensor sensing the radial position and rotational frequency of the rotor; and
a controller operatively coupled to the sensor, wherein the controller is configured to selectively send a current to the second magnetic bearing to change or maintain the radial position and the rotational frequency of the rotor.

2. The device of claim 1, wherein:
the first magnetic bearing comprises first and second permanent magnets; and
the second magnetic bearing comprises a plurality of electromagnetic coils and a pole structure coupled to the rotor; and
the third magnetic bearing comprises the plurality of electromagnetic coils and one of the first or second permanent magnets.

3. The device of claim 1, wherein the first permanent magnet is embedded in the rotor.

4. The device of claim 3, wherein the second permanent magnet is disposed distally relative to the first permanent magnet.

5. The device of claim 3, wherein the second permanent magnet is a ring magnet concentrically disposed relative to the axis.

6. The device of claim 2, wherein the pole structure comprises a first set of permanent sub-magnets circumferentially disposed about a center axis of the rotor.

7. The device of claim 6, wherein the sub-magnets are embedded in the rotor.

8. The device of claim 6, further comprising a second set of permanent sub-magnets circumferentially disposed around the center axis of the rotor, the second set more proximally located on the rotor.

9. The device of claim 6, wherein the sub-magnets are cylindrically shaped and axially magnetized.

10. The device of claim 8, wherein the permanent sub-magnets of the first and second sets are aligned, thereby essentially forming a plurality of vertically arranged pairs of sub-magnets.

11. The device of claim 8, wherein the first and second sets each include at least four sub-magnets.

12. The device of claim 8, wherein the first and second sets each include six sub-magnets.

13. The device of claim 9, wherein an axis of magnetization of the sub-magnets is tangent to an axis of rotation of the rotor.

14. The device of claim 2, wherein the plurality of electromagnetic coils further comprises four vertically arranged pairs of coils circumferentially disposed around the housing.

15. The device of claim 14, wherein each pair of coils is counterwound.

16. The device of claim 1, where the controller is a PID controller.

17. The device of claim 2, wherein the plurality of electromagnetic coils further comprises a plurality of vertically arranged pairs of coils circumferentially disposed around the housing.

18. The device of claim 17, wherein the controller sends a current to a pair of coils to change or maintain the rotational frequency of the rotor.

19. The device of claim 17, wherein the controller sends a current to a pair of coils to change or maintain the radial position of the rotor.

20. The device of claim 17, wherein:
the controller sends a current to diametrically opposed pairs of coils to change or maintain the rotational frequency of the rotor.

21. The device of claim 2, wherein:
the controller sends a current to at least one pair of coils to change the radial position of the rotor.

22. The device of claim 2, wherein the coils magnetically couple to the pole structure when a current is sent to the coils.

23. The device of claim 1, further comprising a pin within the tubular body configured to support the rotor prior to an axial displacement thereof.

24. A device for pumping blood, comprising:
a housing having a distal end adapted to be coupled to a catheter, a proximal end having an outlet, and a tubular body extending between the distal and proximal ends along an axis;
a rotor rotatably disposed within the housing;
a first magnetic bearing further comprising first and second permanent magnets and operative to levitate the rotor to an axial position within the housing;
a second magnetic bearing further comprising a plurality of vertically arranged pairs of electromagnetic coils and a pole structure coupled to the rotor, the second magnetic bearing configured to change or maintain a rotational frequency of the rotor;
a third magnetic bearing further comprising the plurality of vertically arranged pairs of electromagnetic coils and the first permanent magnet, the third magnetic bearing configured to change or maintain a radial position of the rotor;
a Hall Effect sensor sensing the radial position and rotational frequency of the rotor; and
a controller operably coupled to the Hall effect sensor and configured to communicate with the coils to change or maintain the radial position and rotational frequency of the rotor.

* * * * *